(12) United States Patent
Mangels et al.

(10) Patent No.: US 11,833,066 B2
(45) Date of Patent: Dec. 5, 2023

(54) RUNNING BLADE WITH DEPLOYABLE HEEL ATTACHMENT

(71) Applicant: Monarch Assistive Technology, LLC, Independence, MO (US)

(72) Inventors: Cooper D. Mangels, Independence, MO (US); Jacob Overbay, Independence, MO (US)

(73) Assignee: Monarch Assistive Technology, LLC, Independence, MO (US)

( * ) Notice: Subject to any disclaimer, the term of this patent is extended or adjusted under 35 U.S.C. 154(b) by 0 days.

(21) Appl. No.: 17/565,794

(22) Filed: Dec. 30, 2021

(65) Prior Publication Data

US 2022/0202598 A1    Jun. 30, 2022

Related U.S. Application Data

(60) Provisional application No. 63/132,002, filed on Dec. 30, 2020.

(51) Int. Cl.
*A61F 2/66* (2006.01)
*A61F 2/78* (2006.01)
*A61F 2/50* (2006.01)

(52) U.S. Cl.
CPC ............... *A61F 2/66* (2013.01); *A61F 2/78* (2013.01); *A61F 2002/5083* (2013.01); *A61F 2002/665* (2013.01); *A61F 2002/6678* (2013.01)

(58) Field of Classification Search
CPC .. A61F 2/66; A61F 2/6607; A61F 2002/6614; A61F 2002/6621; A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/6692

See application file for complete search history.

(56) References Cited

U.S. PATENT DOCUMENTS

| | | | | |
|---|---|---|---|---|
| 5,571,210 A | * | 11/1996 | Lindh | A61F 2/76 623/53 |
| 5,571,270 A | * | 11/1996 | Larkin | B60D 1/28 280/901 |
| 2010/0332002 A1 | * | 12/2010 | Nelson | A61F 2/66 264/319 |
| 2018/0256369 A1 | * | 9/2018 | Kramer | A61F 2/6607 |

\* cited by examiner

*Primary Examiner* — Bruce E Snow
(74) *Attorney, Agent, or Firm* — Hovey Williams LLP

(57) ABSTRACT

Provided herein is a convertible prosthetic running blade having an adjustable, shiftable heel that can be stowed when running and deployed when walking. The shifting can be performed manually and easily by the wearer without the use of tools. The prosthetic running blade generally comprises a foot body having a toe end and an opposing heel end, and a heel attachment adjacent the heel end, which is shiftable from a running position to a walking position. The foot body is generally in the form of an elongated running blade design, which may have similar shape and construction as traditional c-shape or j-shape running blades, although other shapes and constructions may also be used.

22 Claims, 19 Drawing Sheets

RUNNING BLADE WITH DEPLOYABLE HEEL ATTACHMENT

CROSS-REFERENCE TO RELATED APPLICATIONS

The present application claims the priority benefit of U.S. Provisional Patent Application Ser. No. 63/132,002, filed Dec. 30, 2020, entitled RUNNING BLADE WITH DEPLOYABLE HEEL ATTACHMENT, incorporated by reference in its entirety herein.

BACKGROUND OF THE DISCLOSURE

Field of the Invention

The present invention relates to a prosthetic running blade that is convertible from a running configuration to a walking configuration.

Description of Related Art

Traditional foot prosthetics are designed to be used for either running or walking, but not both. Thus, alternating between running and walking requires amputees to change their prosthesis, or modify it with tools. Existing products are available that claim to perform at various intensity levels, but these fail to operate as optimally as a running blade. However, traditional running blades cause imbalance and discomfort when the amputee is not running. Thus, there is a need for a prosthetic foot that effectively functions as both a running blade and walking foot, combining their strengths, while overcoming the weaknesses of existing designs.

SUMMARY OF THE DISCLOSURE

The present disclosure is broadly concerned with a prosthetic foot that overcomes the deficiencies of traditional prosthetics by having an adjustable, shiftable heel that is stowed when running and deployed when walking. The shifting and stowing can be accomplished manually and easily by the wearer (by hand) without the use of tools, taking only a few seconds. Thus, as used herein, "manual" means the user can shift the heel between the two positions using just their hands without any special tool, such as a wrench, screwdriver, etc. The heel is not removed or detached, but rather shifted and stowed on the blade in a different position (running position) when not in use for walking.

In one embodiment, there is provided a prosthetic running blade comprising a foot body having a toe end and an opposing heel end, and a heel attachment. The heel attachment is adjacent the heel end of the foot body and shiftable from a running position to a walking position.

In another embodiment, there is provided a method of converting a running blade from a walking configuration to a running configuration. The running blade in a walking configuration comprises a foot body having a toe end and an opposing heel end and a heel attachment adjacent the heel end. The heel attachment has at least one surface configured to contact a ground, floor, or other walking surface when in a walking position. The method comprises shifting the heel attachment from the walking position to a running position, whereby the heel attachment is not in contact with the ground, floor or other walking surface, thereby converting the running blade from the walking configuration to the running configuration.

BRIEF DESCRIPTION OF THE DRAWINGS

FIG. 1A shows the running blade in the walking configuration.

FIG. 1B shows the running blade in an intermediate configuration.

FIG. 1C shows the running blade in the running configuration.

FIG. 2A shows the running blade in the walking configuration.

FIG. 2B shows the running blade in an intermediate configuration.

FIG. 2C shows the running blade in the running configuration.

FIG. 3A shows the running blade in the walking configuration.

FIG. 3B shows the running blade in an intermediate configuration.

FIG. 3C shows the running blade in the running configuration.

FIG. 4A shows the running blade in the walking configuration.

FIG. 4B shows the running blade in an intermediate configuration.

FIG. 4C shows the running blade in the running configuration.

FIG. 5A shows the running blade in the walking configuration.

FIG. 5B shows the running blade in an intermediate configuration.

FIG. 5C shows the running blade in the running configuration.

FIG. 6A shows the running blade in the walking configuration.

FIG. 6B shows the running blade in an intermediate configuration.

FIG. 6C shows the running blade in another intermediate configuration.

FIG. 6D shows the running blade in the running configuration.

Figure 1A:
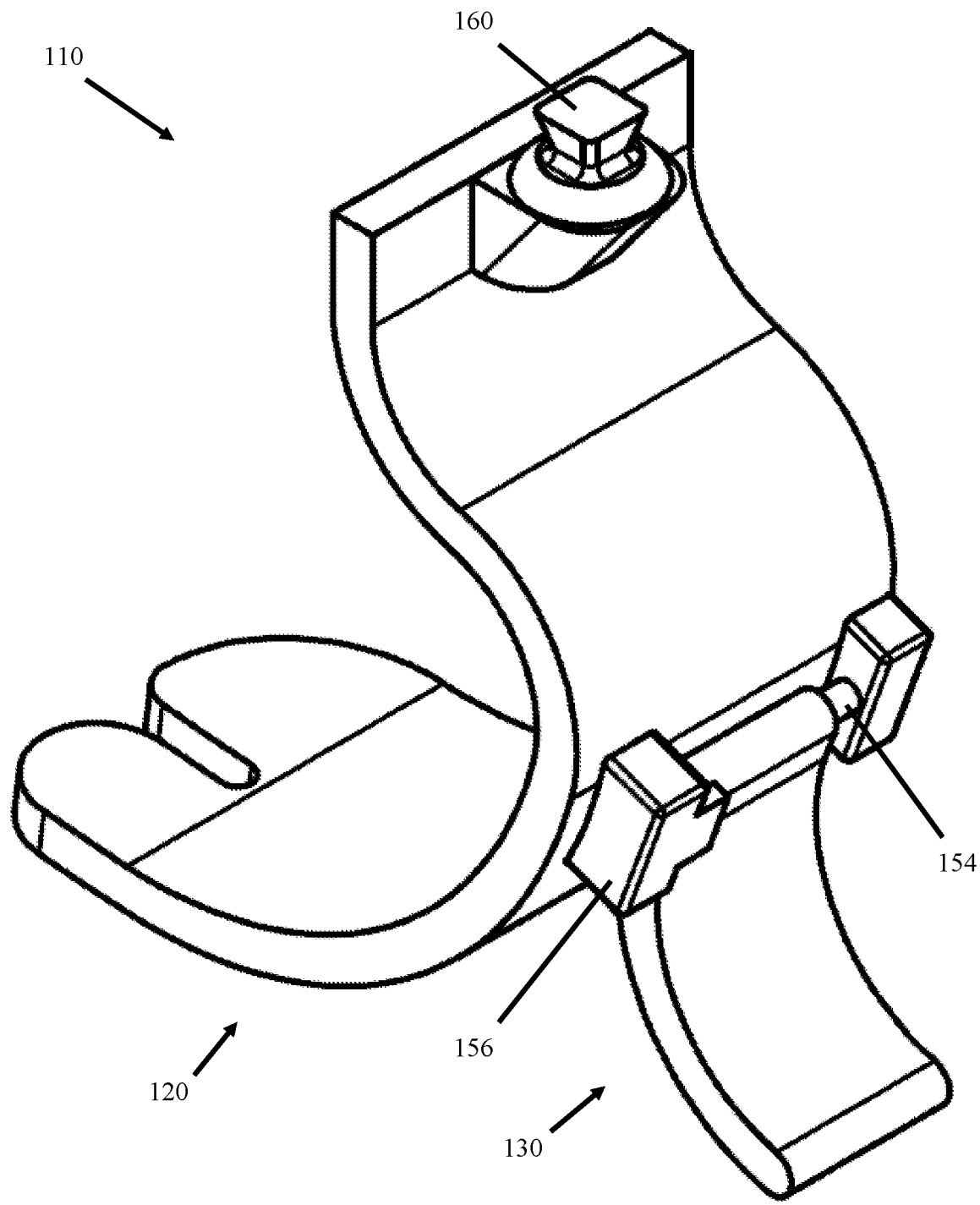
FIGS. 1A-1C show prospective views of a prosthetic running blade according to one embodiment of the present disclosure.

The drawing figures do not limit the present invention to the specific embodiments disclosed and described herein. While the drawings do not necessarily provide exact dimensions or tolerances for the illustrated components or structures, the drawings, not including any purely schematic drawings, are to scale with respect to the relationships between the components of the structures illustrated therein.

DETAILED DESCRIPTION

The present disclosure is concerned with a prosthetic foot, and particularly a running blade, with a deployable (and stowable) heel attachment. The heel attachment is stowed when running to allow the running blade to function optimally, and deployed when not running to provide stability that the running blade alone cannot provide. The prosthetic running blade according to embodiments of the present disclosure generally comprises a foot body having a toe end and an opposing heel end, and a heel attachment adjacent the heel end, which is shiftable from a running position to a walking position.

The foot body is generally in the form of an elongated running blade design, which may have similar shape and construction as traditional c-shape or j-shape running blades. However, the foot body may also have other shapes and constructions in accordance with embodiments of the present disclosure. In certain embodiments, the foot body has a c-shape construct, which may provide optimal propulsion and strength. In certain other embodiments, the foot body has a j-shape construct.

The heel end of the foot body generally comprises an attachment mechanism configured to attach the prosthetic foot to the user, for example, at the ankle, knee, upper leg, or other location. In certain embodiments, the heel end of the foot body comprises a vertical member configured to be inserted into a receiving slot or socket attached to the user, which secures the foot body to the user. In certain embodiments, the heel end of the foot body comprises a pyramid-style projection. Pyramids are standards for the prosthetics industry and can be mounted on top of the running blade for insertion into a prosthetic leg or socket. Various pyramid configurations can be used, as long as they match the point of insertion to the prosthetic leg or socket they are being connected to. In certain embodiments, the foot body comprises a "male" pyramid projection, as shown in the figures. In certain embodiments, the foot body may have a split-toe design at the toe end, which may comprise a cut-in to provide the split-toe geometry, which enables the wearing of sandals and is reminiscent of a human foot in size.

The heel attachment is adjustable and/or shiftable, such that it can be easily stowed when running and deployed when walking. The heel attachment is generally coupled to the foot body behind the running blade (i.e., on an outward surface at the heel end of the foot body) via clips, locks, screws, or other hardware, preventing the heel attachment from unintended or accidental deployment. The heel attachment may have a variety of shapes and constructs. However, in certain embodiments, the heel attachment generally comprises an elongated member having at least one surface configured to contact a floor surface when in the deployed walking position and to be elevated or otherwise positioned so as to not contact the floor surface when in the running position. In certain embodiments, the blade is shiftable from the running configuration to the walking configuration (and vice versa) by vertical rotation (i.e., flipping) of the heel attachment about a horizontal axis, horizontal rotation about a vertical axis, axial rotation, and/or raising/lowering the heel attachment from one position to the other, thus converting the running blade between the walking configuration and the running configuration. In certain embodiments, the heel attachment is shiftable from an inward-angled (toward the foot body) running position to an outward-angled (away from the foot body) walking position thus, converting the running blade between the running configuration and the walking configuration. In certain embodiments, the shifting can be accomplished manually (i.e., by hand without the use of tools), requiring minimal time and effort by the user. In certain embodiments, a spring or other tensioning element may be included, for example, to hold the heel attachment in the desired position. However, other locking mechanisms may also be used to hold the heel attachment in position. In certain embodiments, the shifting moves the contact surface of the heel attachment over a length of about 0.5 inch to about 5 inches, preferably about 1 inch to about 2 inches.

The heel attachment may be coupled to the foot body using a variety of mechanisms, such as exemplified herein. Generally, however, the heel attachment is coupled to the foot body using an attachment assembly that enables the heel attachment to rotate and/or slide between the stowed running position to the deployed walking position, while remaining secured to the foot body without becoming detached.

The foot body, heel attachment, and any other optional components of the prosthetic running blade may be made from a variety of materials. In certain embodiments, the foot body and/or heel attachment comprise carbon fiber. Carbon fiber allows the foot body and heel attachment to be rigid and propulsive. In certain embodiments, the foot body and/or heel attachment comprise one or more materials selected from the group consisting of fiberglass, carbon fiber, composite materials, and combinations thereof. However, the foot body and/or heel attachment may also be made from other materials and combinations of carbon fiber and/or fiberglass with other materials in accordance with embodiments of the present disclosure. In certain embodiments, the attachment assembly and/or pyramid portion of the foot body running blade and the pyramid may comprise a metal-based material, such as titanium or stainless steel, although other metals can also be used provided they have sufficient strength, rust slowly, and have low electrical conductivity. Titanium and stainless steel are particularly preferred. The walking surface/floor contacting surfaces of the running blade may include appropriate coatings or soles, such as rubber, rubberized tread, non-slip gripping materials or grit tape, anti-skid tape, runner soles, sprinter soles, as well as track spikes, and the like.

The prosthetic running blade and its component parts may be manufactured using a variety of methods. In one exemplary embodiment, the foot body may be manufactured by bonding together layers of carbon fiber using an epoxy resin and hardener. The body will typically comprise about 10 to about 150 carbon fiber layers, preferably about 20 to about 120 carbon fiber layers, and more preferably about 30 to about 90 carbon fiber layers. Bubbles may form from the application of resin and hardener. The bubbles can be eliminated by applying heat and pressure, which also thins the layers of resin and hardener. This can be accomplished, for example, via the use of an autoclave. Male pyramid portions, hardware and mechanisms to rotate the heel attachment, and/or the fasteners to attach the running blade to the heel, may be manufactured or purchased separately.

Advantageously, the deployable heel attachment is configured to be retracted and stowed during running such that the heel does not interfere with movement and makes running more efficient. However, when the user desires to walk, the heel attachment can be quickly and easily shifted to the deployed position. Thus, the running blade may be easily converted from a running configuration to a walking configuration without removing or detaching the heel attachment from the running blade (and conversely converted from a running configuration to a walking configuration without removing or detaching the heel attachment from the running blade). This allows for performance at various intensity levels, without requiring separate tools, changing of a worn prosthesis, or purchasing a new one. Additionally, embodiments of the present disclosure allow for manual adjustment without the use of tools. Thus, the heel attachment, as contemplated herein, is not removable and/or detachable and is only contemplated for removal or detachment in the case of replacement/repair (preferably by the manufacturer or other authorized retailer, and not necessarily by the wearer, as special tools may be required to remove and then replace the heel attachment). In other words, in embodiments described herein, the heel attachment is configured to be non-removable by the wearer.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if an apparatus is described as containing or excluding components A, B, and/or C, the apparatus can contain or exclude A alone; B alone; C alone; A and B in combination; A and C in combination; B and C in combination; or A, B, and C in combination.

The preferred forms of the invention described herein are to be used as illustration only, and should not be utilized in a limiting sense in interpreting the scope of the present invention, including modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth various prosthetic running blade designs in accordance with embodiments of the disclosure. It is to be understood, however, that these examples are provided by way of illustration and nothing therein should be taken as a limitation upon the overall scope of the invention. Additionally, it should be understood that the features of each embodiment described below may be included individually or in combination with one or more other features described within the same or other embodiment(s).

Although the figures and description present features of preferred embodiments of the present inventive concept, other preferred embodiments or combinations of certain features from specific embodiments depicted may also be created in keeping with the principles of the invention. Likewise, these other preferred embodiments may in some instances be realized through a combination of features compatible for use together despite having been presented independently in the description or figures.

Furthermore, unless otherwise specified, any directional references (e.g., top, bottom, etc.) are used herein solely for the sake of convenience and should be understood only in relation to each other. For instance, a component might in practice be oriented such that faces referred to as "upper" and "lower" are sideways, angled, inverted, etc. relative to the chosen frame of reference.

Example 1

Figure 1B:
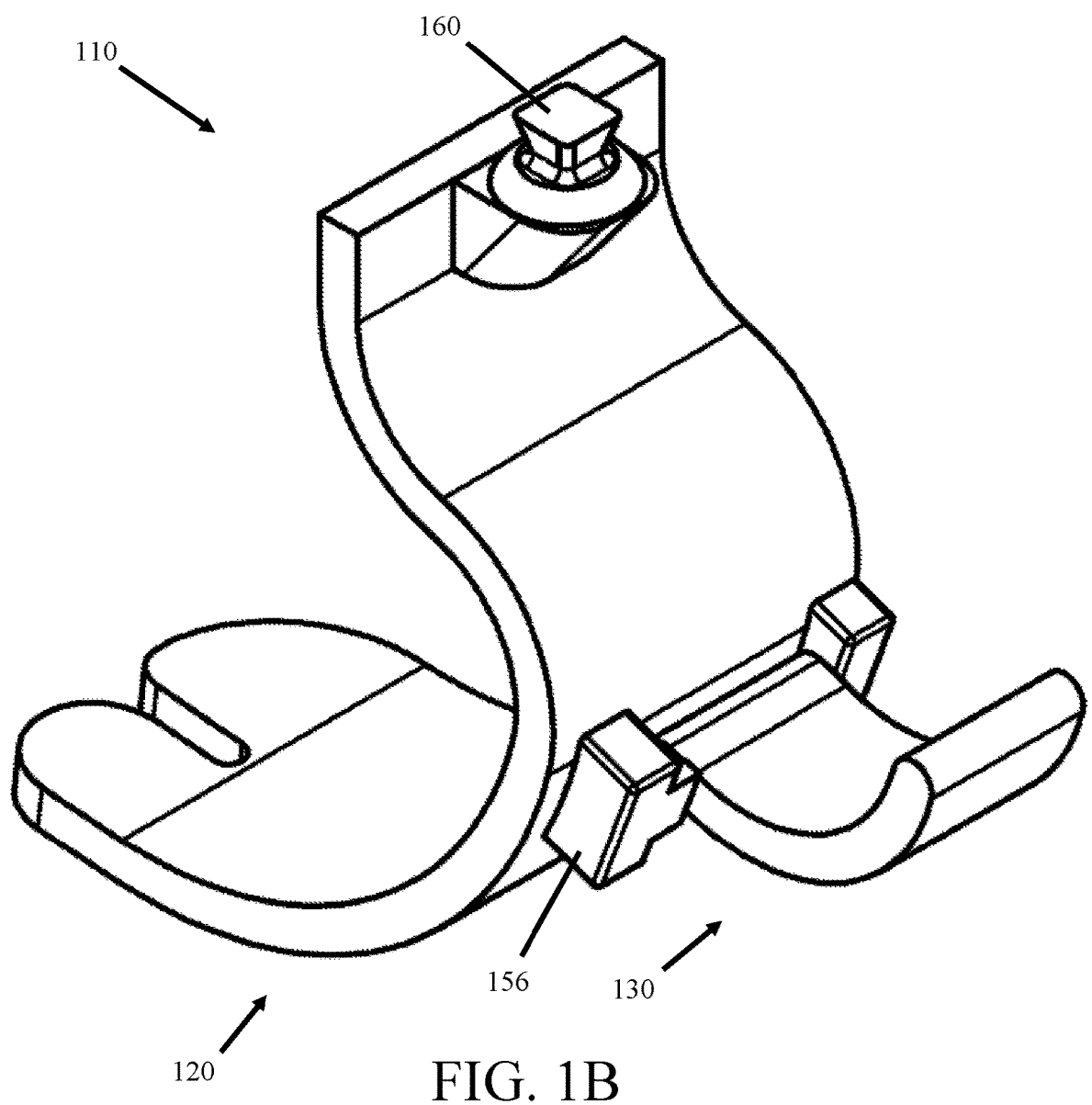
Figure 1C:
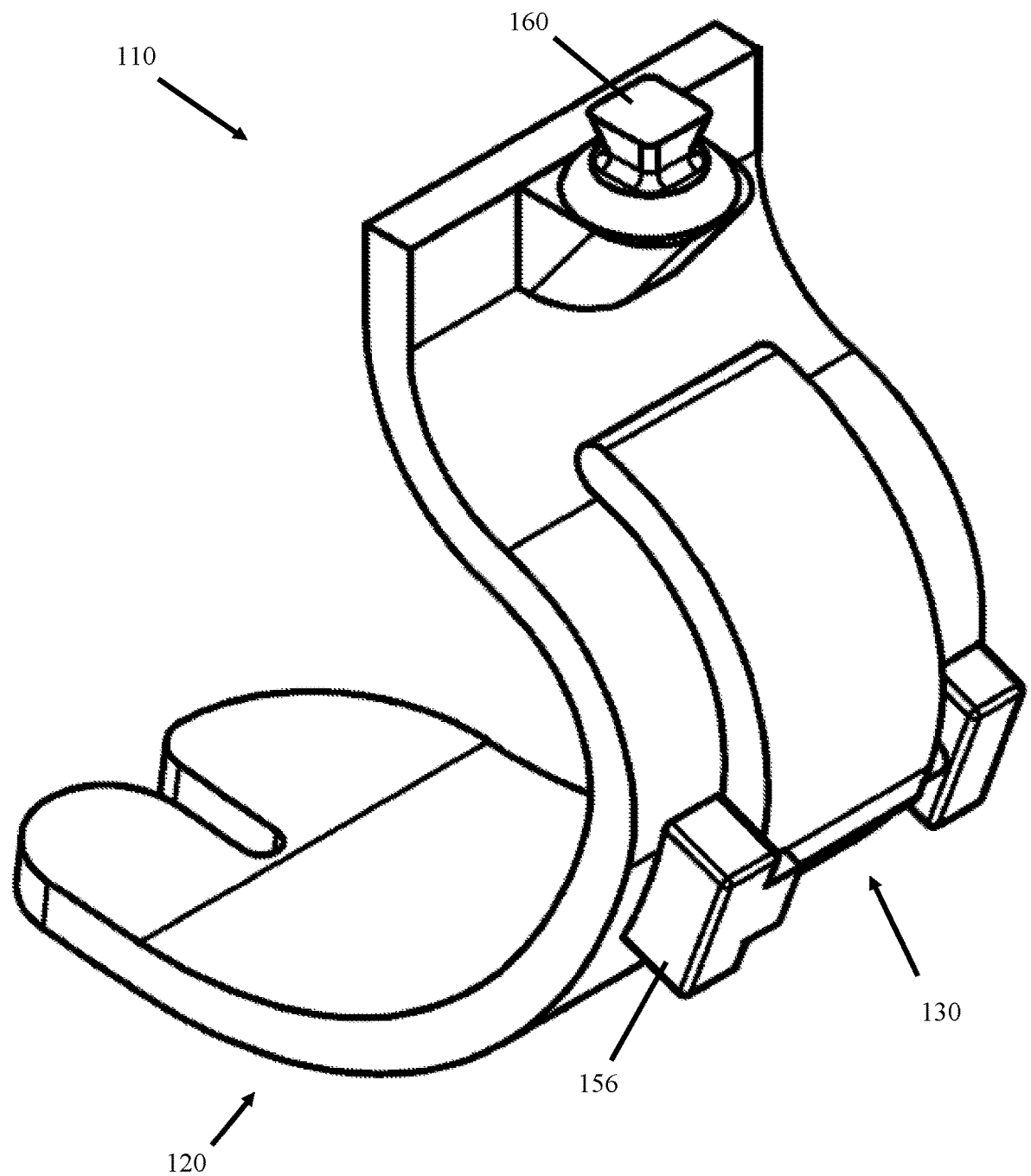

FIGS. 1A-1C show a prosthetic running blade 110 comprising a generally j-shaped foot body 120 and a heel attachment 130. As shown, the heel attachment 130 may have a generally curved shape, although uncurved and other designs may also be used. Heel attachment 130 is generally configured to rotate around a horizontal axis directly behind the middle portion (on the heel end) of the j-shaped foot body 120. The heel attachment 130 may be rotatably coupled to a rod 154 secured to the body 120. A clip 156 may be positioned at one side of the rod 154 to hold the heel attachment 130 in the desired position and to inhibit or prevent the heel attachment 130 from rotating out of position. A spring (not shown) may be equipped on the rod 154 to push and hold the heel attachment 130 horizontally in the clip 156. A male pyramid connector 160 may be affixed to the top of the foot body 120 to install the running blade onto a corresponding socket, mount, or other mechanism secured to the user.

FIG. 1A shows running blade 110 in its walking configuration, with the heel attachment 130 deployed in the walking position such that the bottom portion of the heel attachment 130 is rotated outward and configured to contact the ground, floor, or other walking surface. In use, running blade 110 may be converted by the user from walking configuration to running configuration by sliding the heel attachment 130 to the side (out of the clip 156), rotating the heel attachment 130 upward, for example about 180 degrees around the horizontal axis of rod 154, and sliding the heel attachment 130 back into the clip 156. When the rod 154 is equipped with a spring, sliding the heel attachment 130 away from the clip 156 loads the spring, and thus, after rotation, the heel attachment 130 can slide back into the clip 156 by simply releasing the heel attachment 130 and allowing the spring to push the heel attachment back into the clip 156. FIG. 1B shows running blade 110 in an intermediate configuration with heel attachment 130 slid away from the clip 156 and being rotated upward. FIG. 1C shows running blade 110 in its running configuration, with heel attachment 130 secured in the running position such that the bottom portion of the heel attachment 130 is rotated upward and positioned adjacent the foot body 120. The user may convert running blade 110 from its running configuration back to its walking configuration by sliding the heel attachment 130 to the side, rotating downward, and sliding the heel attachment 130 back into the clip 156.

Example 2

Figure 2A:
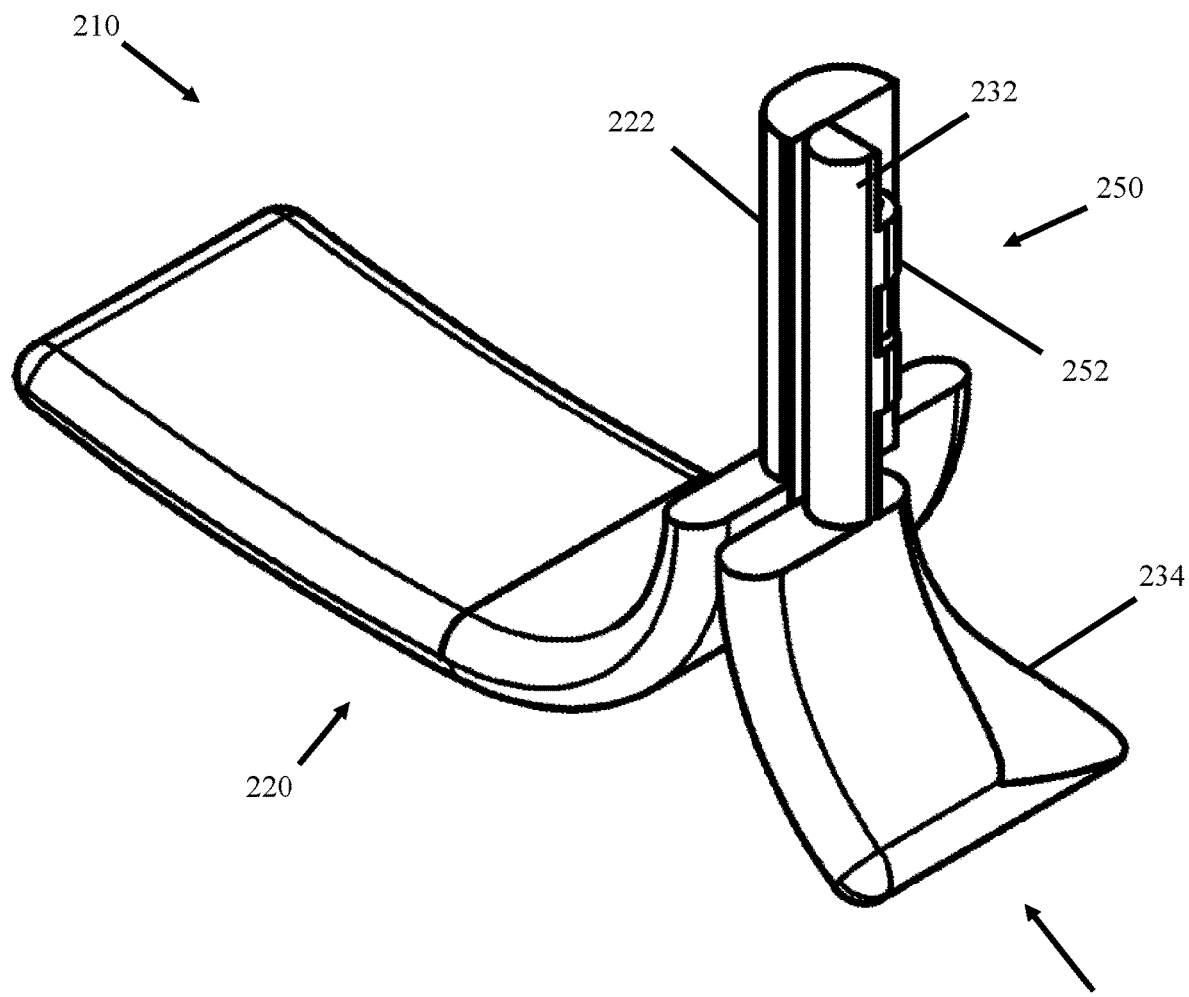
FIGS. 2A-2C show prospective views of a prosthetic running blade according to one embodiment of the present disclosure.
Figure 2B:
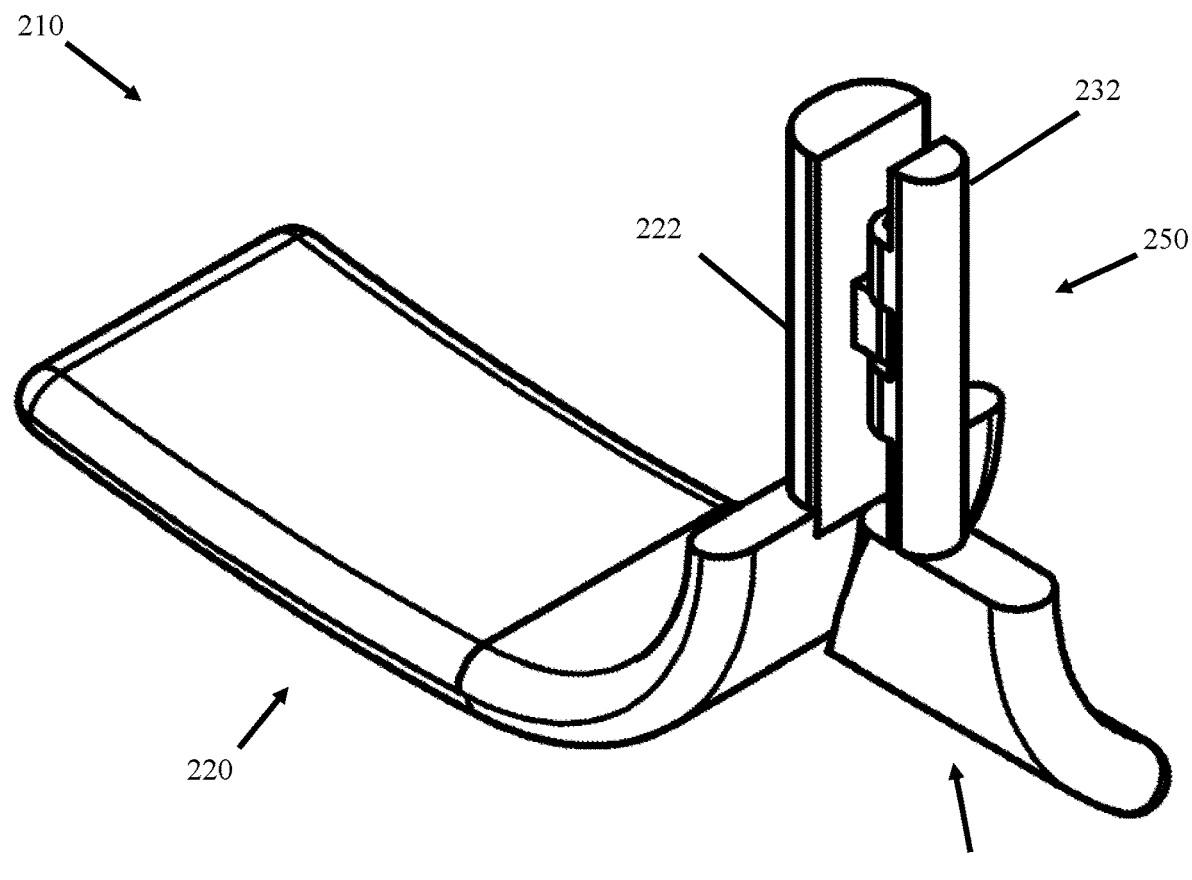
Figure 2C:
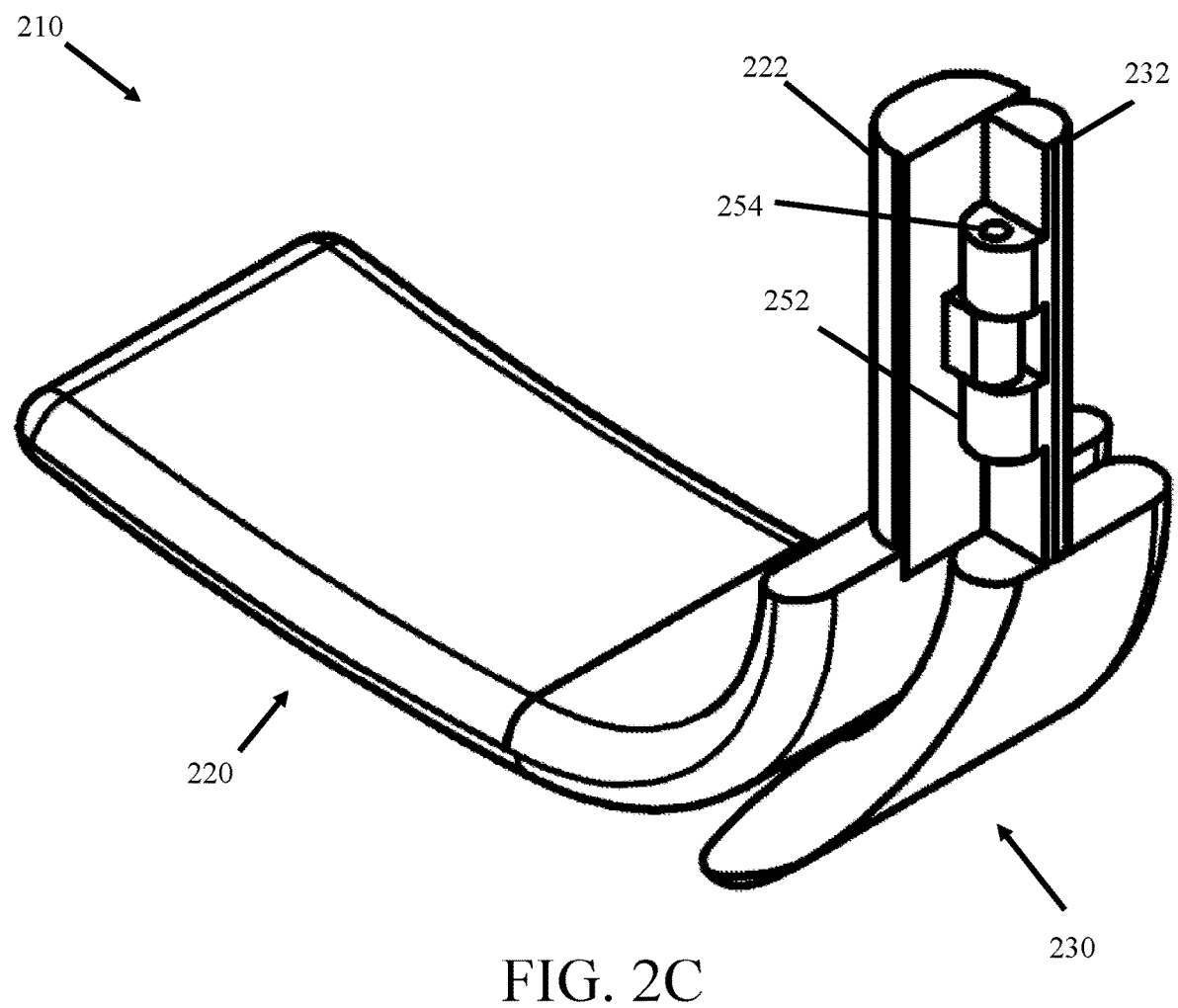

FIGS. 2A-2C show a prosthetic running blade 210 comprising a generally j-shaped foot body 220 and a generally scoop-shaped heel attachment 230. Heel attachment 230 is generally configured to rotate around a vertical axis directly behind the vertical portion of the j-shaped foot body 220. Foot body 220 may comprise a top projection 222 rotatably coupled to a corresponding top projection 232 on the heel attachment 230. The top projections 222, 232 may be rotatably coupled by a hinge 250, comprising appropriate knuckles 252 and a pin 254, or similar mechanism. In certain embodiments, heel attachment 230 may comprise a corner cut out 234 to allow about 180-degree rotation around the vertical axis. A locking mechanism (not shown) can be included and used to ensure the heel attachment 230 remains in its desired position. In certain embodiments, the vertical portion of the foot body 220 may be thinner than the horizontal portion that contacts the ground, floor, or other surface, which allows the vertical portion to be inserted into a cylindrical leg cover to protect and cover the inner workings and connections.

FIG. 2A shows running blade 210 in its walking configuration, with the heel attachment 230 deployed in the walking position such that the bottom portion of the heel attachment 230 is rotated outward and configured to contact the ground. In use, running blade 210 may be converted by the user from walking configuration to running configuration by rotating heel attachment 230. FIG. 2B shows running blade 210 in an intermediate configuration with the heel attachment 230 being rotated. FIG. 2C shows running blade 210 in its running configuration, with heel attachment 230 secured in the running position such that the bottom portion of the heel attachment 230 is rotated inward adjacent the foot body 220. The user may convert running blade 210 from its running configuration back to its walking configuration by rotating the heel attachment in the opposite direction.

Example 3

Figure 3A:
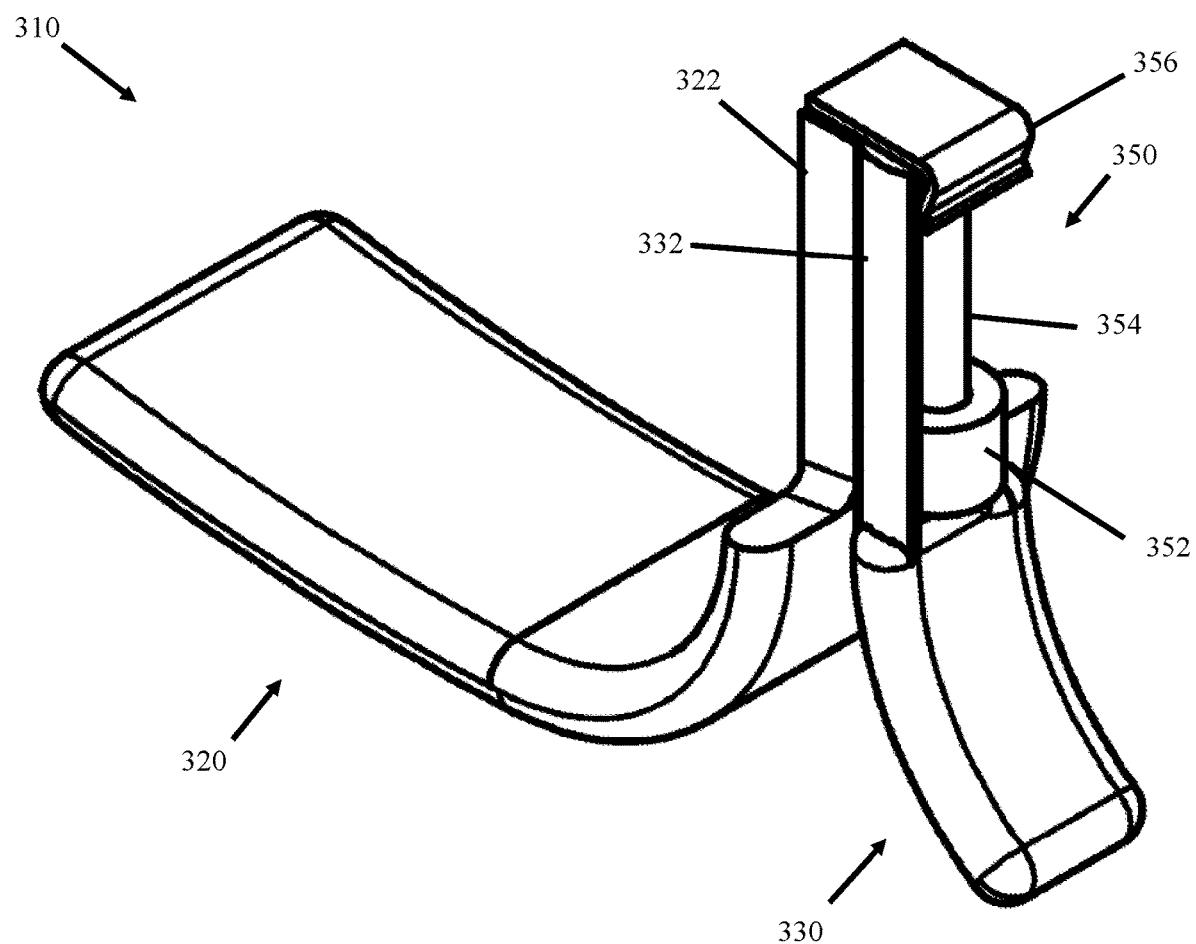
FIGS. 3A-3C show prospective views of a prosthetic running blade according to one embodiment of the present disclosure.
Figure 3B:
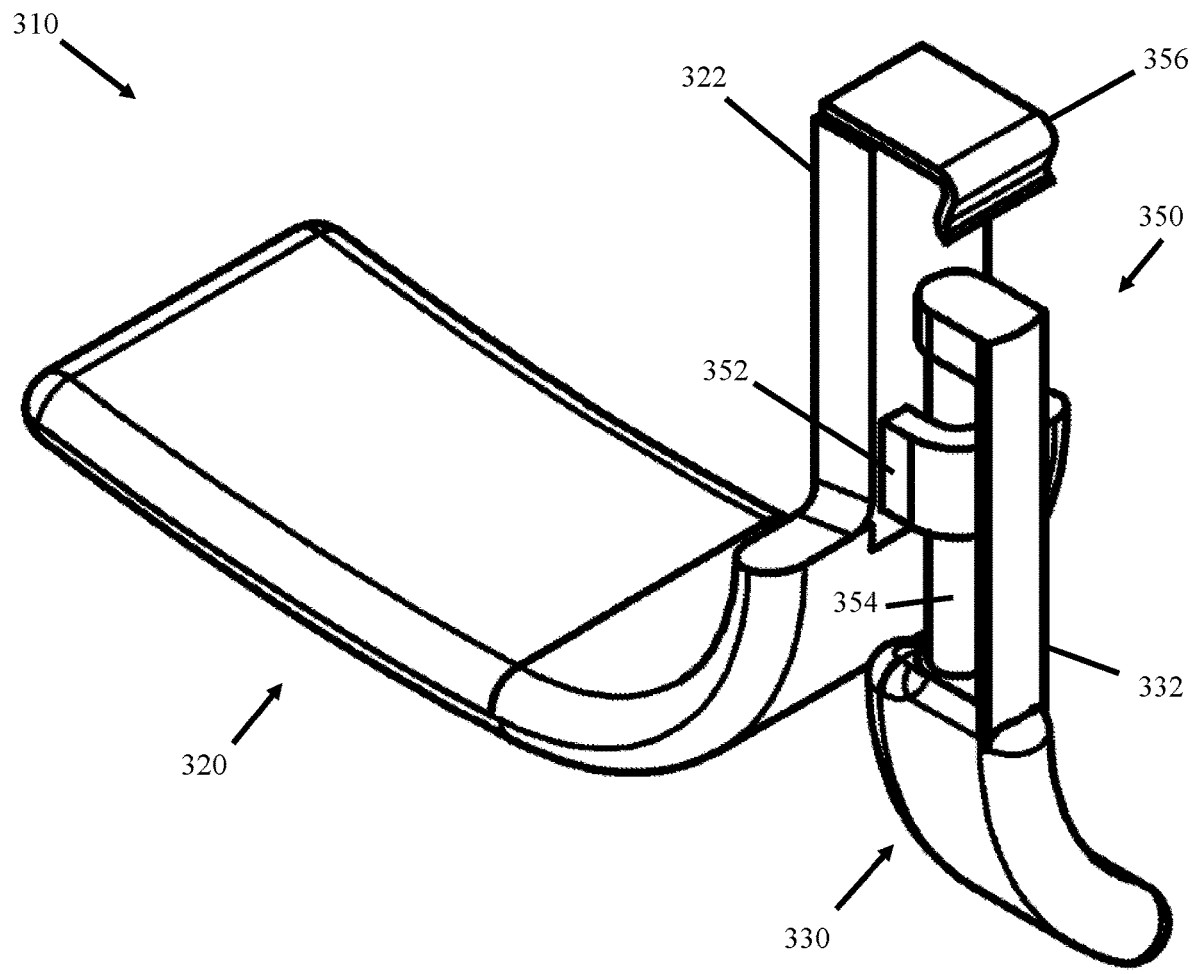
Figure 3C:
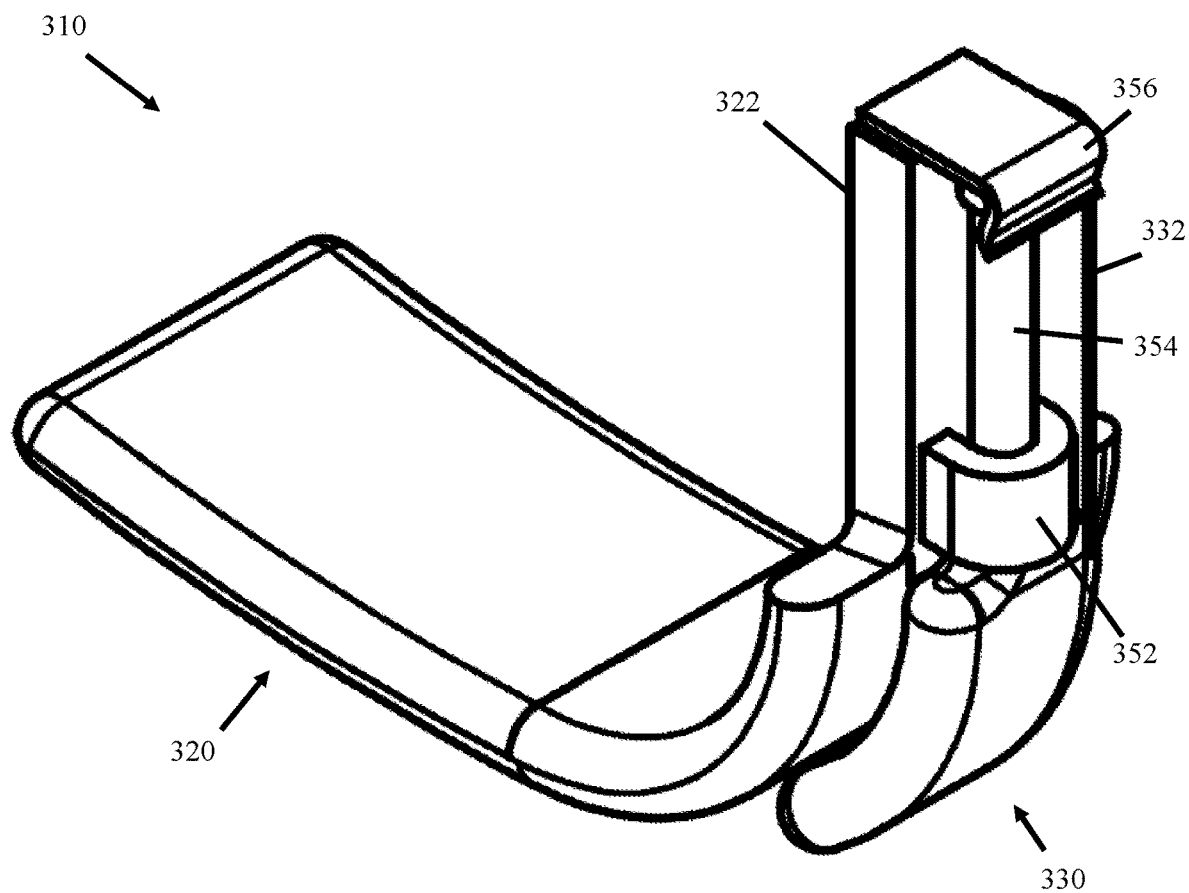

FIGS. 3A-3C show a prosthetic running blade 310 comprising a generally j-shaped foot body 320 and a heel attachment 330. Heel attachment 330 may have a curved or scooped shape and is generally configured to rotate around a vertical axis directly behind the vertical portion of the j-shaped foot body 320. Foot body 320 may comprise a top projection 322 rotatably and slidably coupled to a corresponding top projection 332 on the heel attachment 330. The top projections 322, 332 may be rotatably coupled by a rotating slide lock mechanism 350 comprising guide 352, pin 354, and a clip 356 positioned at the top of the foot body projection 322. Clip 356 is configured to hold heel attachment 330 in either the running position or the walking position and to prevent the heel attachment 330 from rotating out of the desired position. A spring (not shown) may be included in slide lock mechanism 350 to push and hold the pin 354 of heel attachment 330 up into the clip 356.

FIG. 3A shows running blade 310 in its walking configuration, with the heel attachment 330 deployed in the walking position such that the bottom portion of the heel attachment 330 is rotated outward and configured to contact the ground. In use, running blade 310 may be converted by the user from walking configuration to running configuration by lowering (e.g., pulling/pushing down) pin 354 of the heel attachment 330 out of the clip 356, rotating the heel attachment 330, for example about 180 degrees, and raising (e.g., pulling/pushing up) the pin 354 of the heel attachment 330 back up into the clip 356. When the rotating slide lock mechanism 350 includes a spring, lowering the pin 354 loads the spring, and thus, after rotation, the pin 354 can be raised by simply releasing the pin 354 and allowing the spring to push the pin 354 back into the clip 356. FIG. 3B shows running blade 310 in an intermediate configuration with heel attachment 330 lowered and being rotated. FIG. 3C shows running blade 310 in its running configuration, with heel attachment 330 secured in the running position such that the bottom portion of the heel attachment 330 is rotated inward adjacent the foot body 320. The user may convert running blade 310 from its running configuration back to its walking configuration by lowering, rotating, and raising the heel attachment 330 (rotating in the opposite direction).

Example 4

Figure 4A:
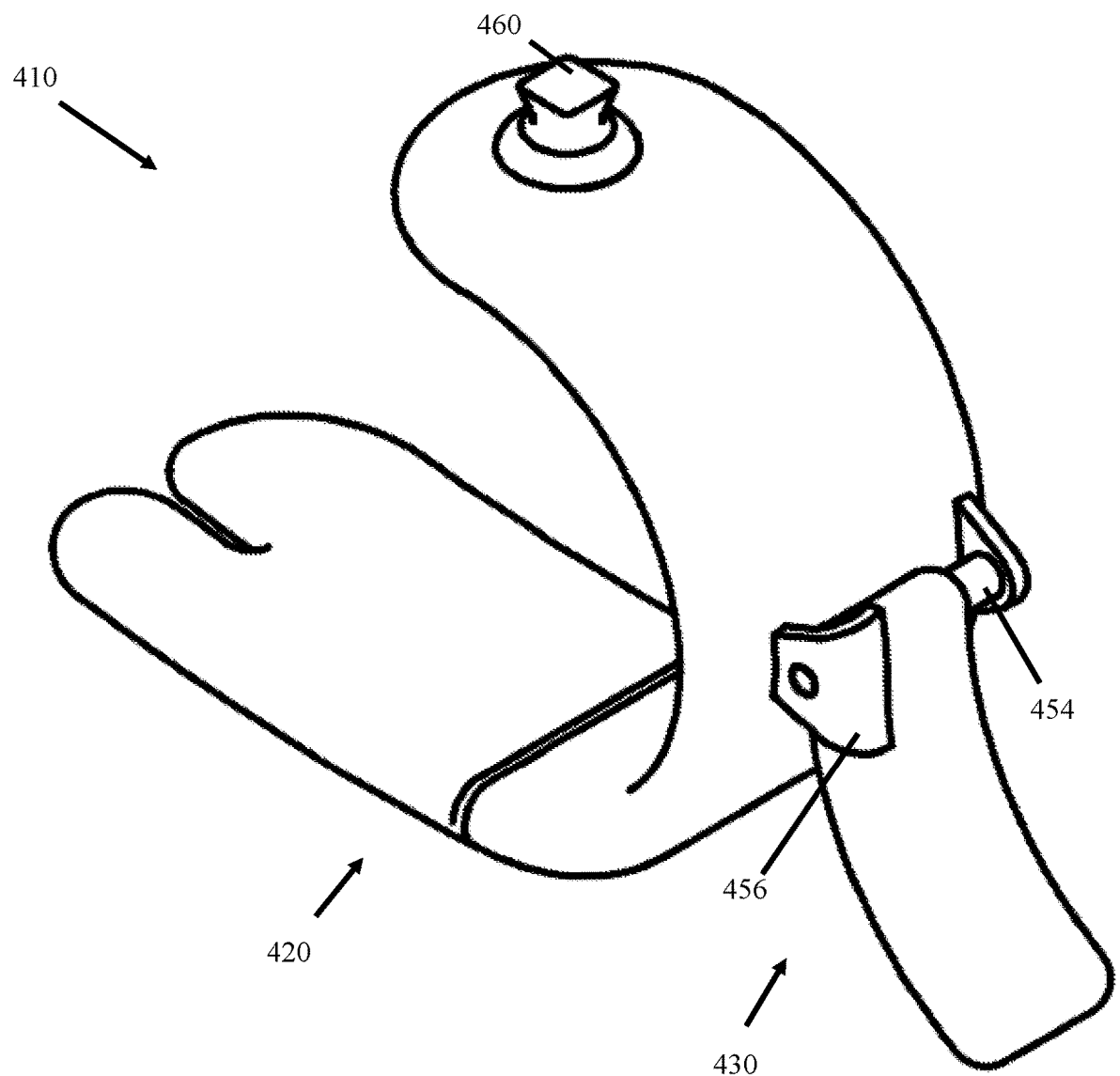
FIGS. 4A-4C show prospective views of a prosthetic running blade according to one embodiment of the present disclosure.
Figure 4B:
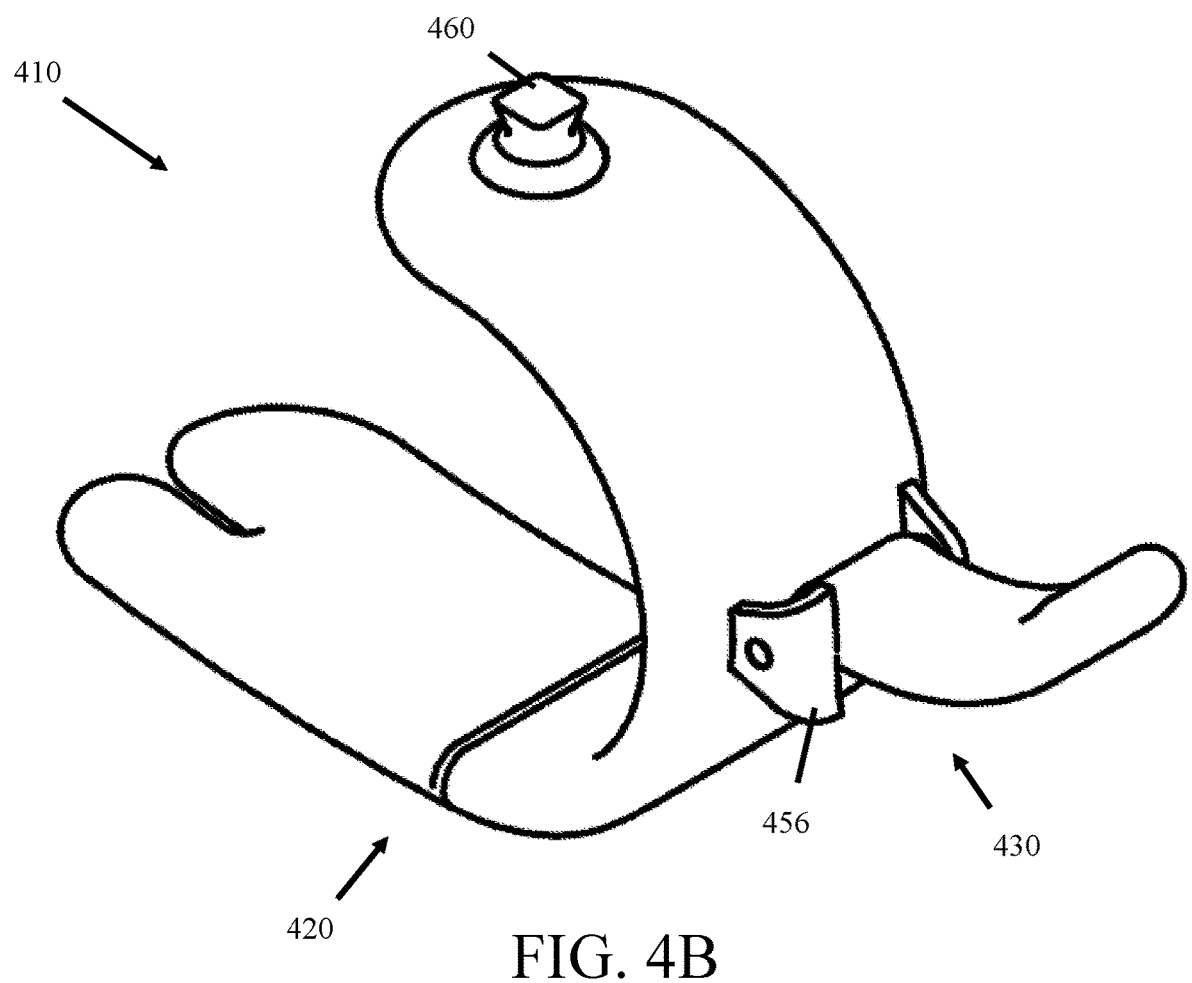
Figure 4C:
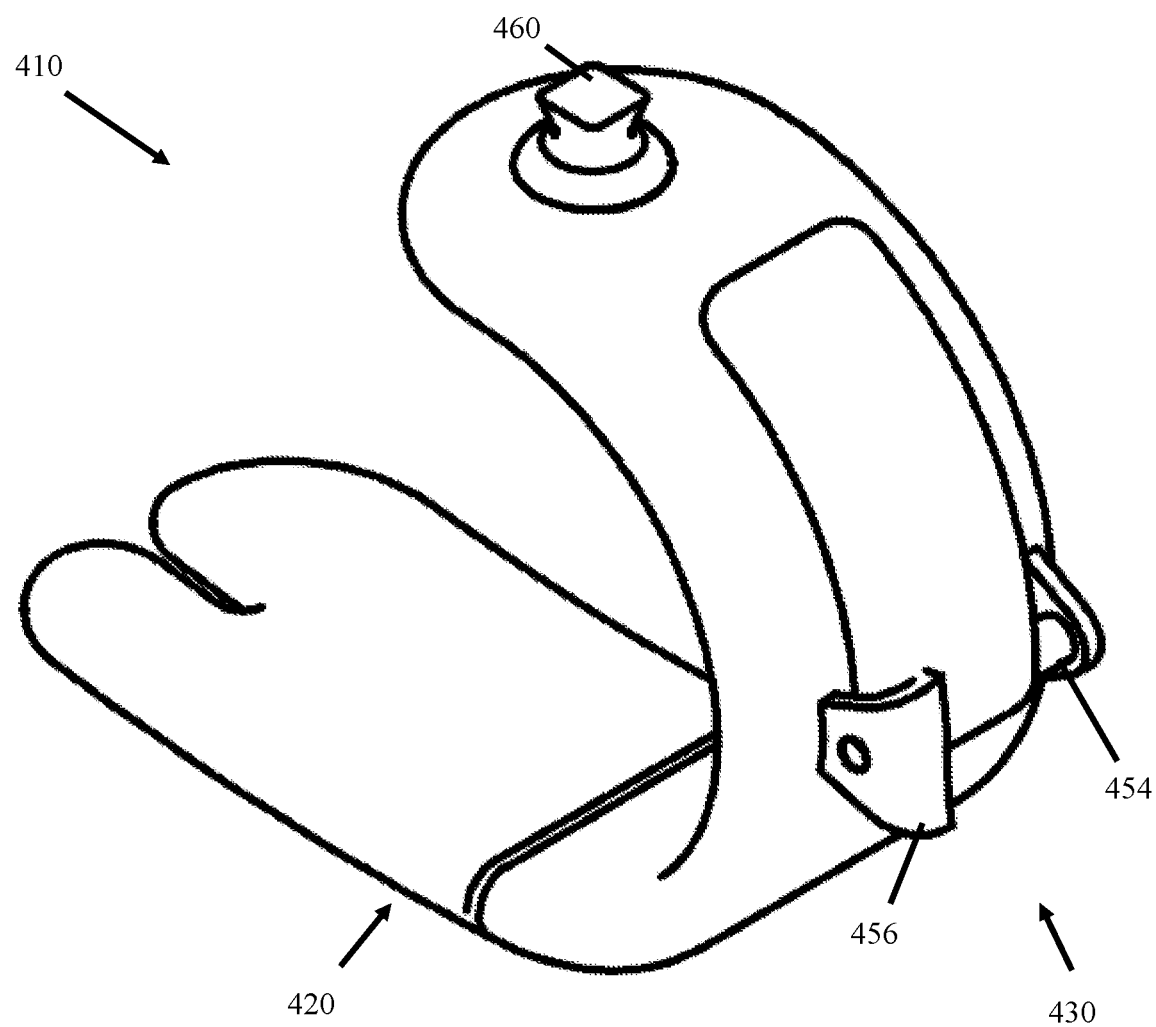

FIGS. 4A-4C show a prosthetic running blade 410 comprising a generally c-shaped foot body 420 and a heel attachment 430. Heel attachment 430 is similar in structure and function to heel attachment 130 shown in FIGS. 1A-1C. Heel attachment 430 may have a curved or scooped shape and is generally configured to rotate around a horizontal axis directly behind the middle portion of the c-shaped foot body 420. The heel attachment 430 may be rotatably coupled to a rod 454 secured to the body 420. A clip 456 may be positioned at one side of the rod 454 to hold the heel attachment in the desired position and to inhibit the heel attachment 430 from rotating out of position. A spring (not shown) may be equipped on the rod 454 to push and hold the heel attachment 430 horizontally in the clip 456. A male pyramid connector 460 may be affixed to the top of the foot body 420 to install the running blade onto a corresponding socket, mount, or other mechanism secured to the user.

FIG. 4A shows running blade 410 in its walking configuration, with the heel attachment 430 deployed in the walking position such that the bottom portion of the heel attachment 430 is rotated outward and configured to contact the ground. In use, running blade 410 may be converted by the user from walking configuration to running configuration by sliding the heel attachment 430 to the side (out of the clip 456), rotating the heel attachment 430 upward, for example about 180 degrees around the horizontal axis of rod 454, and sliding the heel attachment 430 back into the clip 456. When the rod 454 is equipped with a spring, sliding the heel attachment 430 away from the clip 456 loads the spring, and thus, after rotation, the heel attachment 430 can slide back into the clip 456 by simply releasing the heel attachment 430 and allowing the spring to push the heel attachment back into the clip 456. FIG. 4B shows running blade 410 in an intermediate configuration with the heel attachment 430 slid away from the clip 456 and being rotated upward. FIG. 4C shows running blade 410 in its running configuration, with heel attachment 430 secured in the running position such that the bottom portion of the heel attachment 430 is rotated upward and positioned adjacent the foot body 420. The user may convert running blade 410 from its running configuration back to its walking configuration by sliding the heel attachment 430 to the side, rotating downward, and sliding the heel attachment 430 back into the clip 456.

Example 5

Figure 5A:
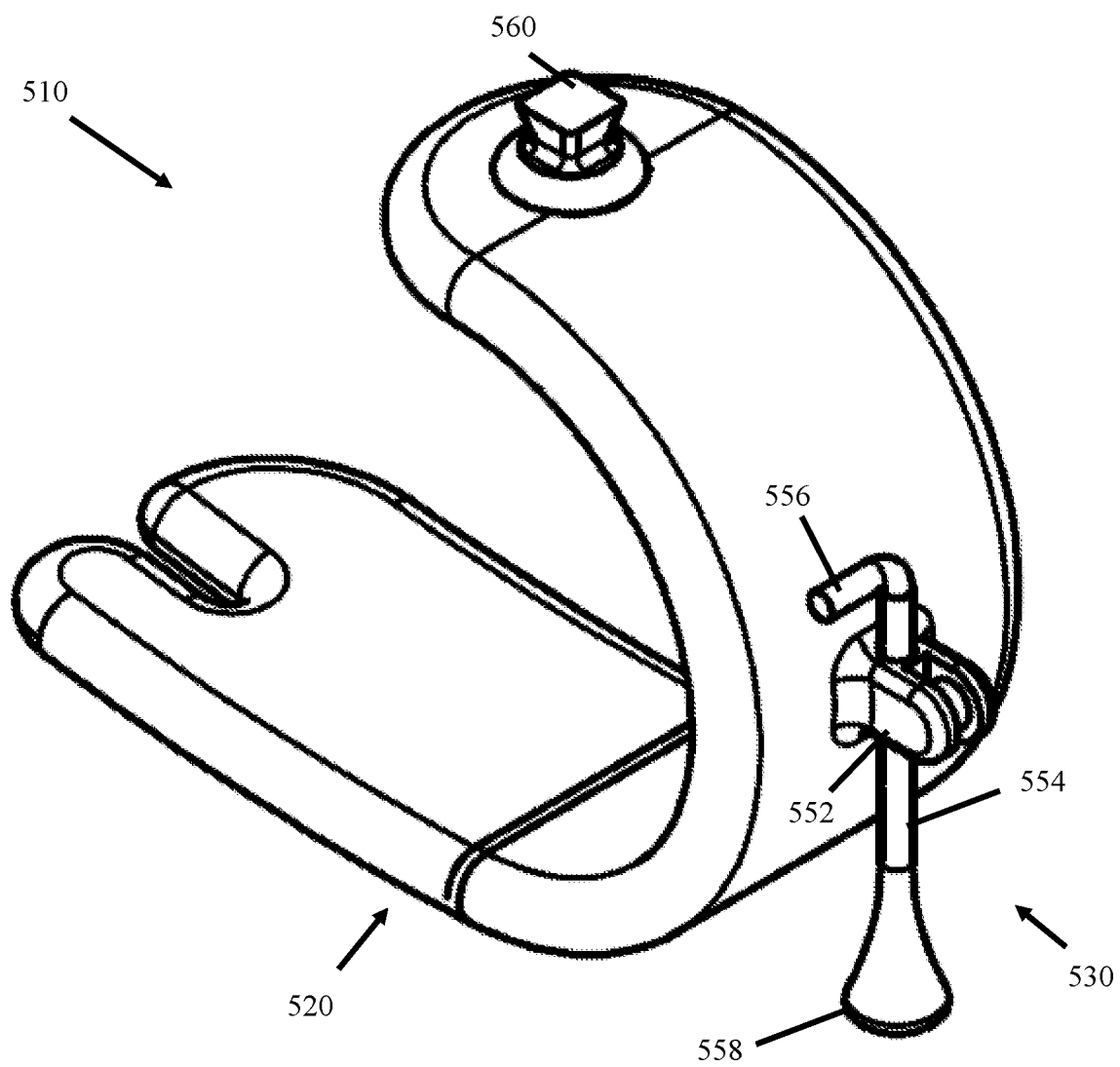
FIGS. 5A-5C show prospective views of a prosthetic running blade according to one embodiment of the present disclosure.
Figure 5B:
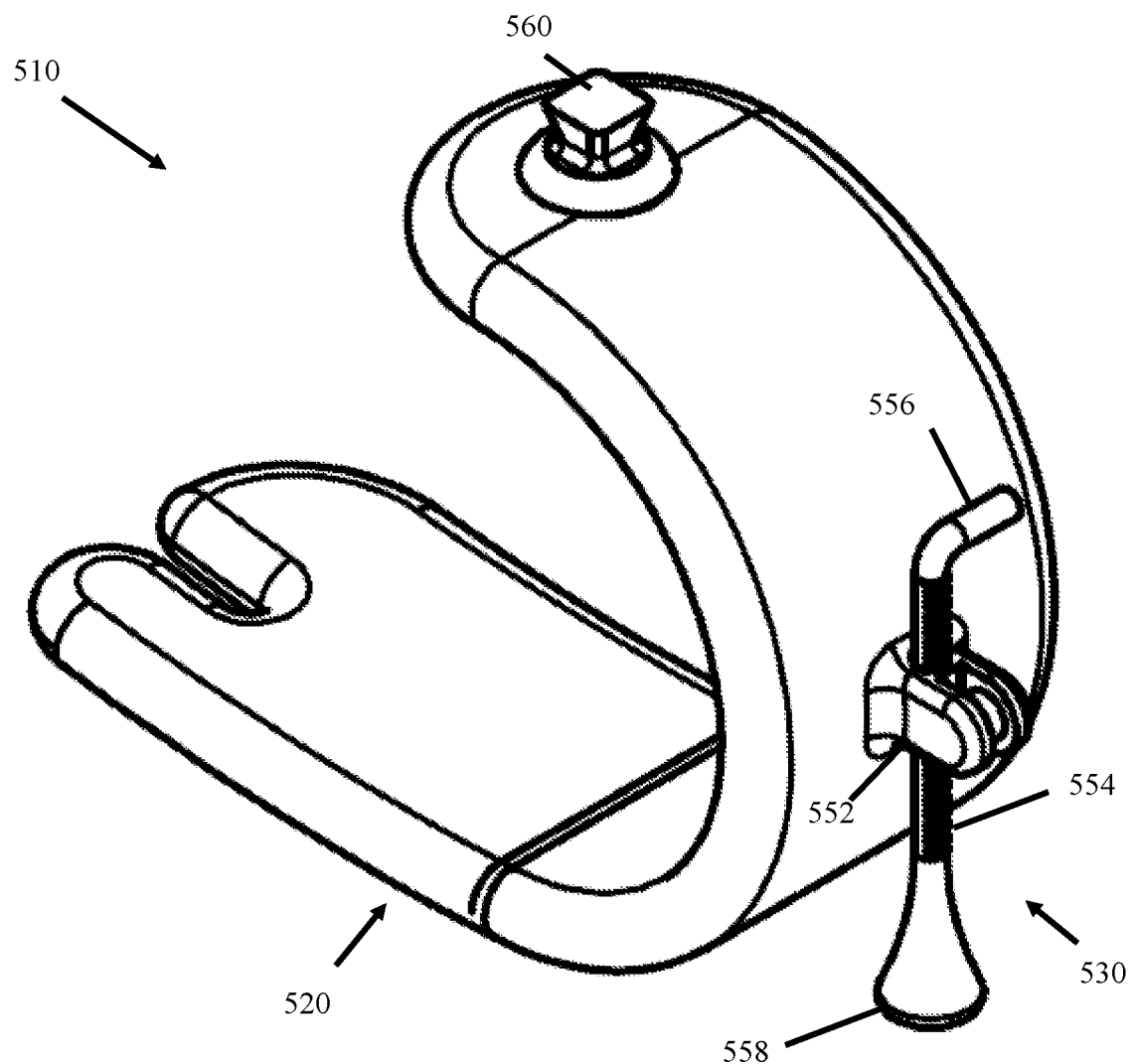
Figure 5C:
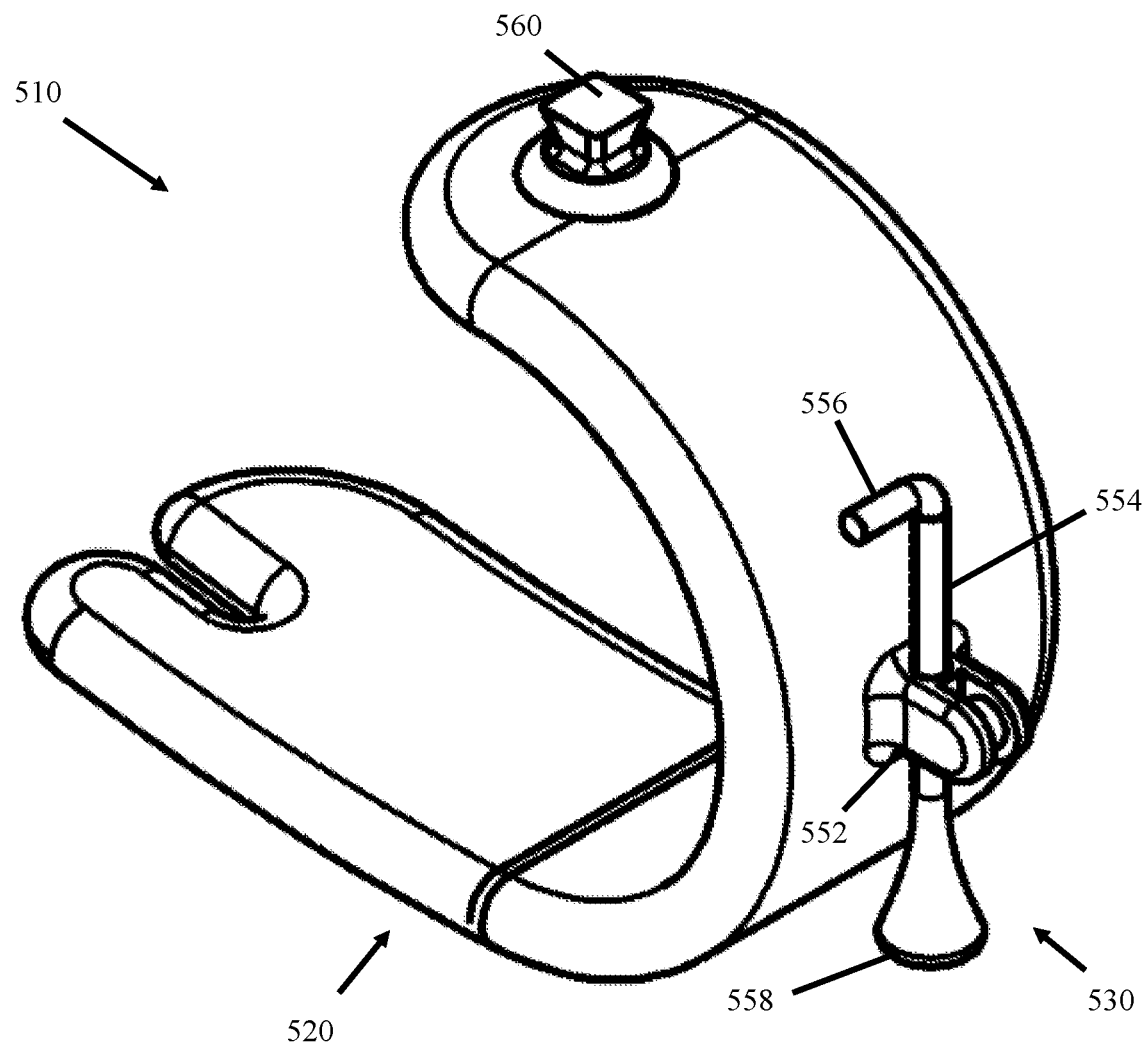

FIGS. 5A-5C show a prosthetic running blade 510 comprising a generally c-shaped foot body 520 and a heel attachment 530. As shown, heel attachment 530 may comprise a notched rod 554 that can be shifted up and down through a guide 552 comprising a loaded torsion spring (ratcheting mechanism) attached to the back of the c-shaped foot body 520. The rod 554 is configured to rotate, for example using a handle 556 located at the top of the rod 554, to engage or disengage the notches to prevent or allow the rod 554 to move up and down within the guide 552. A pliable material tip 558 may be affixed to the bottom end of the rod 554 to reduce or prevent damage due to impact. A male pyramid connector 560 may be affixed to the top of the foot body 520 to install the running blade onto a corresponding socket, mount, or other mechanism secured to the user.

FIG. 5A shows running blade 510 in its walking configuration, with the heel attachment 530 deployed in the walking position such that the bottom end of the heel attachment 430 is rotated outward and configured to contact the ground, floor, or other surface. In use, running blade 510 may be converted by the user from walking configuration to running configuration by rotating the rod 554, for example axially about 180 degrees, to disengage the spring from the notches, and then sliding (e.g., pushing or pulling) the rod 554 up into the desired position (i.e., away from the walking surface). The rod 554 is then rotated back, for example axially 180 degrees in the opposite direction, to engage the spring in the notches. FIG. 4B shows running blade 510 in an intermediate configuration with heel attachment 530 rotated about 180 degrees such that the spring has been disengaged from the notches. FIG. 4C shows running blade 510 in its running configuration, with heel attachment 530 raised and rotated in the running positioned such that the bottom portion of the heel attachment 530 is raised away from the surface and the spring is reengaged in the notches. The user may convert running blade 510 from its running configuration back to its walking configuration by rotating the heel attachment 530, sliding the rod 554 downward, and rotating the heel attachment 530 back such that the spring reengages the notches.

Example 6

FIGS. 6A-6D show a prosthetic running blade 610 comprising a generally c-shaped foot body 620 and heel attachment 630. Heel attachment 630 is similar in structure to heel attachment 130 shown in FIGS. 1A-1C. Heel attachment 630 may have a curved or scooped shape and is generally configured to rotate around a horizontal axis directly behind the middle portion of the c-shaped foot body 620. As shown, the curved heel attachment is generally configured to rotate up and away (from the floor, ground, or other surface) and down and out (toward the floor, ground, or other surface). The heel attachment 630 may be rotatably coupled to a rod secured to the body 620. A latch bar 656 may be affixed around the point of rotation with a hinge 658 on one side and a locking mechanism 659 on the other side. The latch bar 656 is configured to hold the heel attachment 630 in the desired position and to inhibit or prevent the heel attachment 630 from rotating out of position when closed and locked. However, when the latch bar 656 is open, the heel attachment 630 is allowed to rotate and does not require the use of a spring. A male pyramid connector 660 may be affixed to the top of the foot body 620 to install the running blade onto a corresponding socket, mount, or other mechanism secured to the user.

Figure 6A:
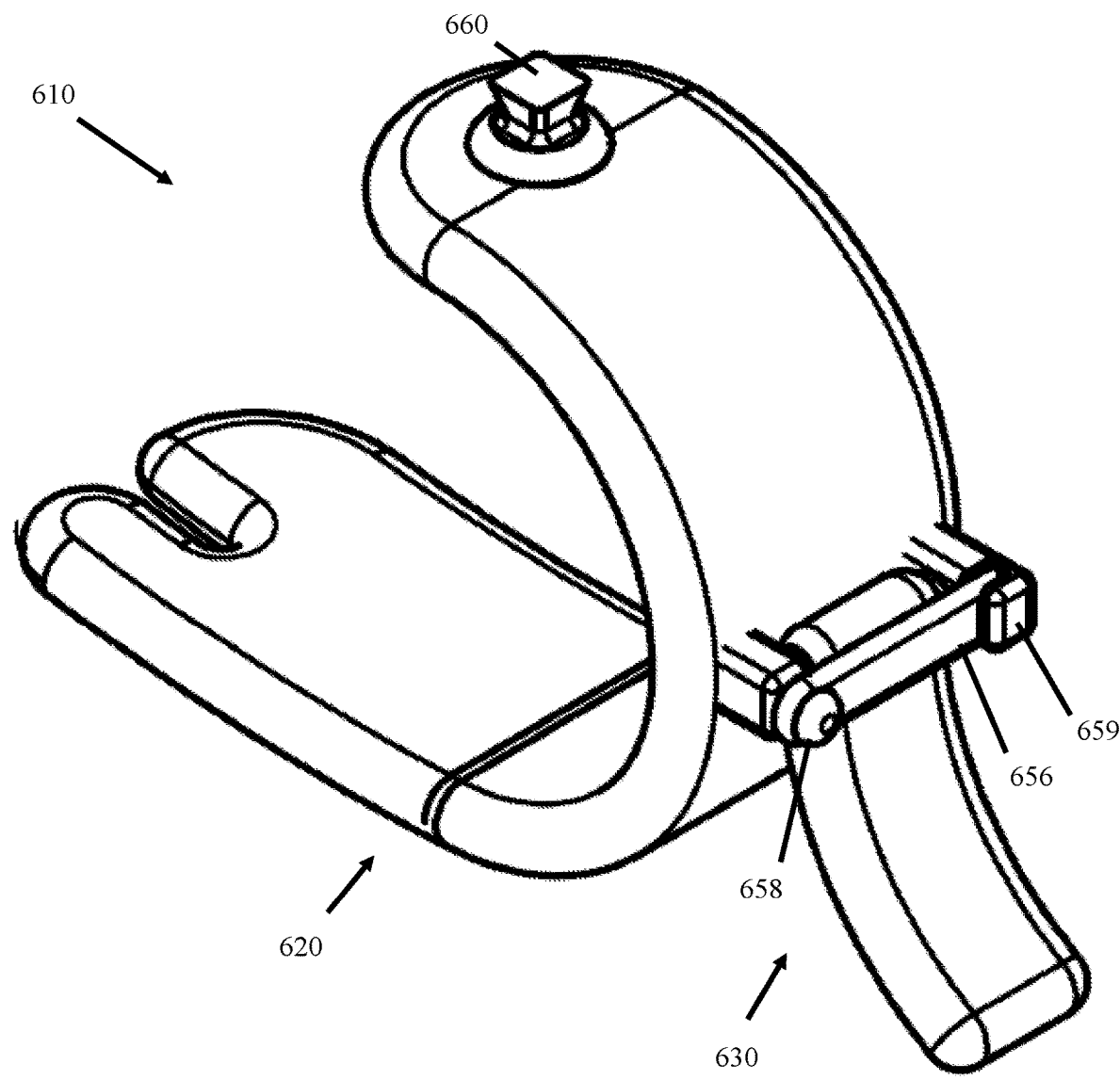
FIGS. 6A-6D show prospective views of a prosthetic running blade according to one embodiment of the present disclosure.
Figure 6B:
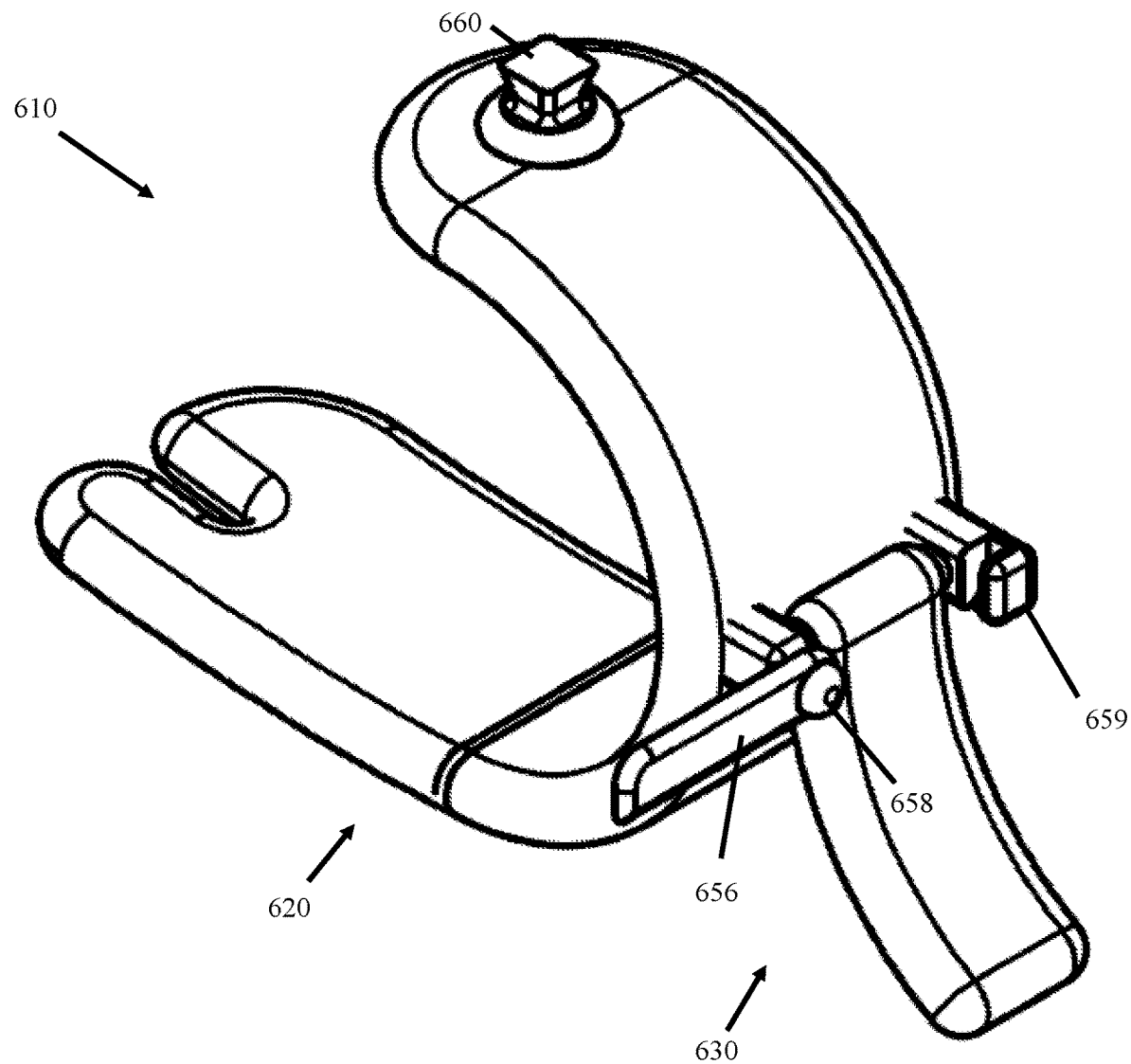
Figure 6C:
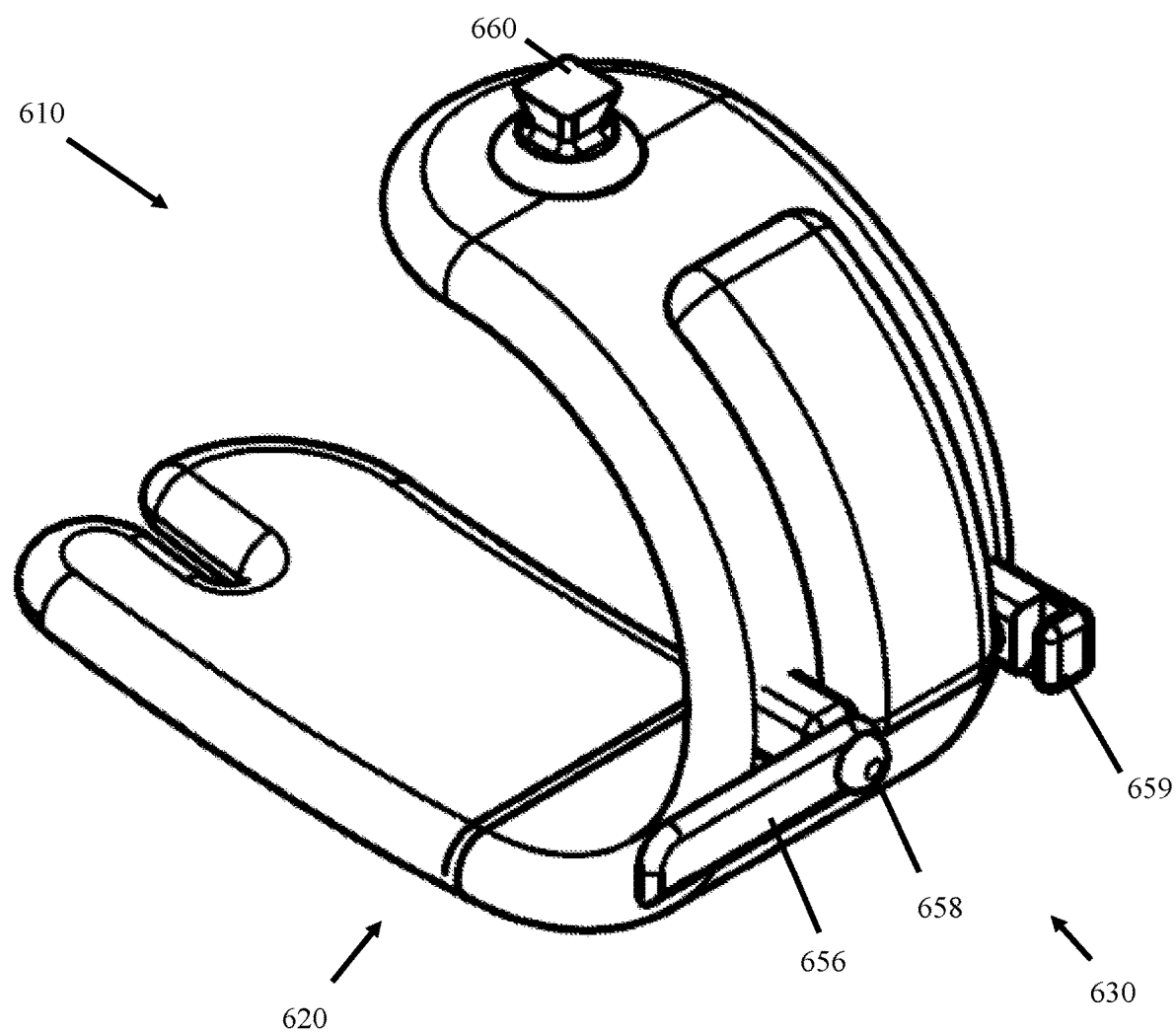
Figure 6D:
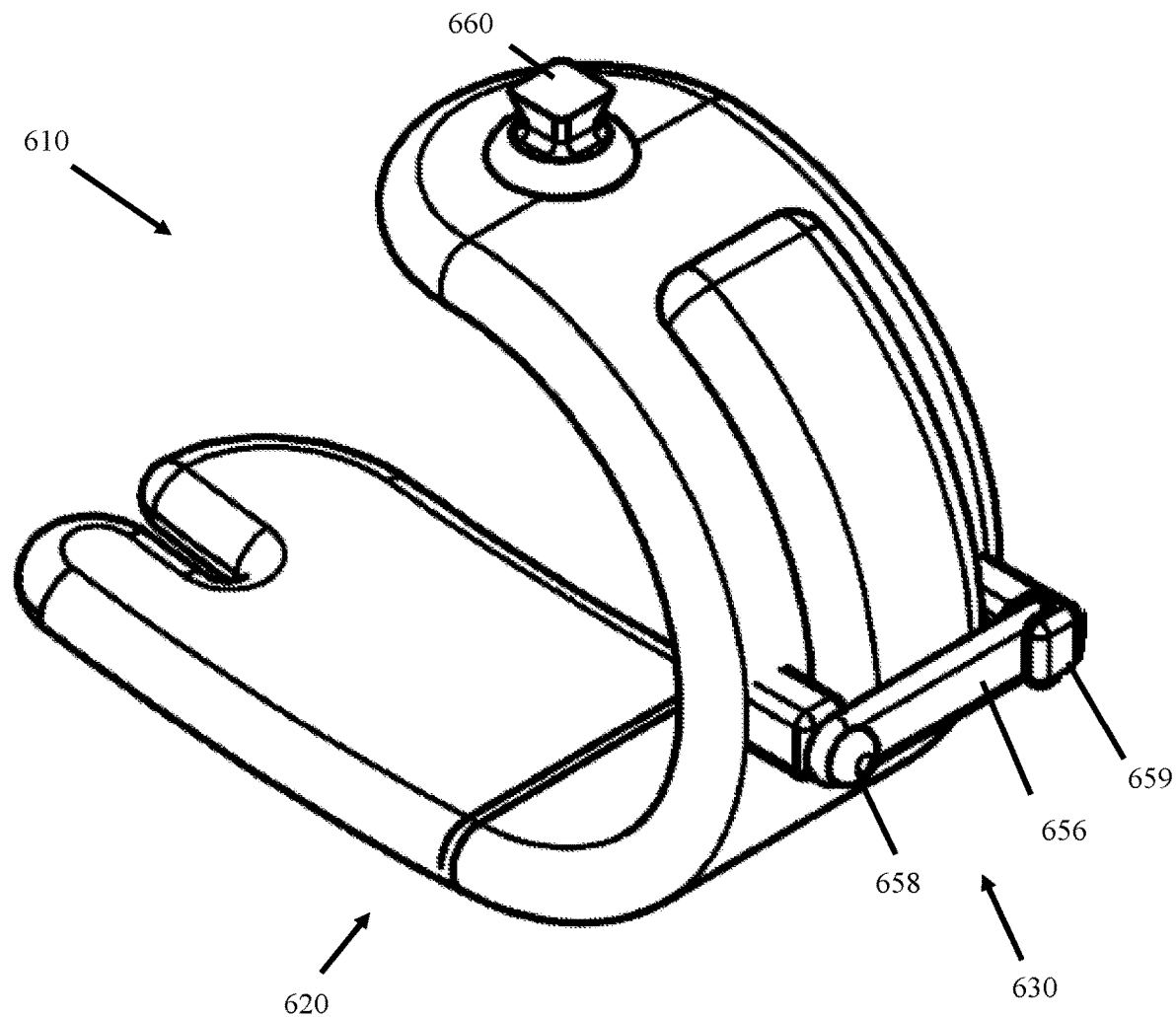

FIG. 6A shows running blade 610 in its walking configuration, with the heel attachment 630 deployed in the walking position such that the bottom end of the heel attachment 630 is rotated outward and configured to contact the ground, floor, or other surface. In use, running blade 610 may be converted by the user from walking configuration to running configuration by unlocking and opening the latch bar 656. The heel attachment can then be rotated, for example about 180 degrees around the horizontal axis, and the latch bar 656 can be closed and locked. FIG. 6B shows running blade 610 in an intermediate configuration with the latch bar 656 open and unlocked. FIG. 6C shows running blade 610 in another intermediate configuration with the latch bar 656 still unlocked and the heel attachment 630 rotated upward. FIG. 6D shows running blade 610 in its running configuration, with the latch bar 656 closed and locked, and the heel attachment 630 secured in the running position such that the bottom portion of the heel attachment 430 is rotated upward and positioned adjacent the foot body 620. The user may convert running blade 610 from its running configuration back to its walking configuration by opening the latch bar 656, rotating the heel attachment 630 downward, and closing and locking the latch bar 656.

The invention claimed is:

1. A convertible prosthetic running blade having a running configuration and a walking configuration, said prosthetic running blade comprising:
   a foot body having a toe end and an opposing heel end; and
   a heel attachment adjacent the heel end and manually shiftable from a running position to a walking position to thereby convert the running blade from the running configuration to the walking configuration,
   wherein the heel attachment comprises an elongated member having at least one surface configured to contact a ground, floor, or other walking surface when in the walking position and to be elevated or otherwise positioned so as to not contact the surface when in the running position, and
   wherein the elongated member is curved outward from the foot body when the heel attachment is in the walking position and curved toward the foot body when the heel attachment is in the running position.

2. The prosthetic running blade of claim 1, wherein the foot body has a generally j-shape or c-shape construct.

3. The prosthetic running blade of claim 1, wherein the foot body comprises a horizontal rod positioned adjacent the heel end, wherein the elongated member is rotatably coupled to the horizontal rod and configured to rotate upward into the running position and downward into the walking position.

4. The prosthetic running blade of claim 3, wherein the heel attachment comprises a clip positioned at one side of the rod configured to hold the elongated member in the walking position or in the running position.

5. The prosthetic running blade of claim 4, wherein the heel attachment comprises a spring equipped on the rod and configured to push and hold the heel attachment horizontally within the clip.

6. The prosthetic running blade of claim 1, further comprising a pyramid connector affixed to the top of the foot body and configured to install the running blade onto a corresponding socket, mount, or other mechanism secured to a user.

7. The prosthetic running blade of claim 1, wherein the foot body comprises one or more materials selected from the group consisting of fiberglass, carbon fiber, and combinations thereof.

8. The prosthetic running blade of claim 1, wherein the heel attachment comprises one or more materials selected from the group consisting of fiberglass, carbon fiber, and combinations thereof.

9. The prosthetic running blade of claim 8, wherein the foot body comprises about 10 to about 150 layers of bonded carbon fiber layers.

10. The prosthetic running blade of claim 9, wherein the foot body is formed by bonding together the layers of carbon fiber using an epoxy resin and hardener.

11. The prosthetic running blade of claim 1, wherein the foot body comprises a cut-in at the toe end defining a split-toe geometry.

12. The prosthetic running blade of claim 1, wherein the elongated member is rotatably coupled around a vertical axis adjacent the heel end of the foot body, wherein the elongated member is configured to rotate outward from the foot body in the walking position to contact said ground, floor or other walking surface and rotate inward and curved toward the foot body in the running position so as not to contact aid ground, floor or other walking surface.

13. A method of converting a running blade from a walking configuration to a running configuration, wherein the running blade in a walking configuration comprises a foot body having a toe end and an opposing heel end and a heel attachment adjacent the heel end, said heel attachment comprising an elongated member having at least one surface configured to contact a ground, floor, or other walking surface when in a walking position, wherein the elongated member is curved outward from the foot body when the heel attachment is in the walking position, said method comprising:

manually shifting the heel attachment from said walking position to a running position by rotating said heel attachment such that the elongated member is curved toward the foot body in the running position, whereby said heel attachment is not in contact with said ground, floor or other walking surface, thereby converting the running blade from the walking configuration to the running configuration.

14. The method of claim 13, wherein said heel attachment is shiftably stowed on said running blade in said running position.

15. The method of claim 13, wherein the foot body comprises a horizontal rod positioned adjacent the heel end, wherein the heel attachment comprises an elongated member rotatably coupled to the horizontal rod.

16. The method of claim 15, wherein the shifting step comprises rotating the elongated member from the downward walking position to an upward running position, thereby converting the running blade from a walking configuration to a running configuration.

17. The method of claim 15, wherein the rotating moves the at least one contact surface of the elongated member over a length of about 0.5 inch to about 5 inches.

18. The method of claim 15, wherein the heel attachment further comprises a clip positioned at one side of the rod configured to hold the elongated member in the walking position or in the running position, wherein the method further comprises sliding the elongated member horizontally out of the clip before the rotating and sliding the elongated member horizontally back into the clip after the rotating.

19. The method of claim 18, wherein the heel attachment further comprises a spring equipped on the rod, wherein sliding the elongated member out of the clip loads the spring, and wherein the elongated member slides back into the clip under the force of the spring.

20. A convertible prosthetic running blade having a running configuration and a walking configuration, said prosthetic running blade comprising:

a foot body having a toe end and an opposing heel end; and a heel attachment adjacent the heel end and shiftable from a running position to a walking position to thereby convert the running blade from the running configuration to the walking configuration, wherein the heel attachment comprises an elongated member having at least one surface configured to contact a ground, floor, or other walking surface when in the walking position and to be elevated or otherwise positioned so as to not contact the surface when in the running position, wherein the elongated member is curved outward from the foot body when the heel attachment is in the walking position and curved toward the foot body when the heel attachment is in the running position.

21. A convertible prosthetic running blade having a running configuration and a walking configuration, said prosthetic running blade comprising:

a foot body having a toe end and an opposing heel end; and a heel attachment adjacent the heel end and shiftable from a running position to a walking position to thereby convert the running blade from the running configuration to the walking configuration, wherein the heel attachment comprises an elongated member having at least one surface configured to contact a ground, floor, or other walking surface when in the walking position and to be elevated or otherwise positioned so as to not contact the surface when in the running position, wherein the elongated member is rotatably coupled around a horizontal axis adjacent the heel end of the foot body, wherein the elongated member is configured to rotate upward into the running position and downward into the walking position.

22. A method of converting a running blade from a walking configuration to a running configuration, wherein the running blade in a walking configuration comprises a foot body having a toe end and an opposing heel end and a heel attachment adjacent the heel end, said heel attachment comprising an elongated member having at least one surface configured to contact a ground, floor, or other walking surface when in a walking position, said method comprising:

shifting the heel attachment from said walking position to a running position whereby said heel attachment is not in contact with said ground, floor or other walking surface, thereby converting the running blade from the walking configuration to the running configuration, wherein the elongated member is rotatably coupled around a horizontal axis adjacent the heel end of the foot body, wherein the elongated member is configured to rotate upward into the running position and downward into the walking position.

* * * * *